United States Patent
Jass et al.

(10) Patent No.: US 7,345,191 B2
(45) Date of Patent: Mar. 18, 2008

(54) PROCESS FOR PREPARATION OF PROBUCOL DERIVATIVES

(75) Inventors: Paul Alan Jass, Charles City, IA (US); Jason Scott Douglas, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 498 days.

(21) Appl. No.: 11/069,455

(22) Filed: Feb. 26, 2005

(65) Prior Publication Data
US 2006/0194875 A1     Aug. 31, 2006

(51) Int. Cl.
*C07C 9/00* (2006.01)
*C07C 321/00* (2006.01)
*A01N 37/10* (2006.01)

(52) U.S. Cl. .................. 560/142; 562/431; 514/543; 560/142

(58) Field of Classification Search ............... 560/142; 562/431; 514/543
See application file for complete search history.

(56) References Cited

U.S. PATENT DOCUMENTS

| | | | |
|---|---|---|---|
| 5,262,439 A | 11/1993 | Parthasaratay | |
| 5,380,747 A | 1/1995 | Medford et al. | |
| 5,750,351 A | 5/1998 | Medford et al. | |
| 5,773,209 A | 6/1998 | Medford et al. | |
| 5,807,884 A | 9/1998 | Medford et al. | |
| 5,811,449 A | 9/1998 | Medford et al. | |
| 5,846,959 A | 12/1998 | Medford et al. | |
| 5,877,203 A | 3/1999 | Medford et al. | |
| 6,323,359 B1 * | 11/2001 | Jass | 560/142 |
| 6,548,699 B1 | 4/2003 | Sommers | |

* cited by examiner

*Primary Examiner*—Joseph K. McKane
*Assistant Examiner*—Janet L. Coppins
(74) *Attorney, Agent, or Firm*—Richard J. Hammond

(57) ABSTRACT

A method is described for the preparation of polymorphic forms of water-soluble derivatives of probucol compounds having the following formula Formula 2

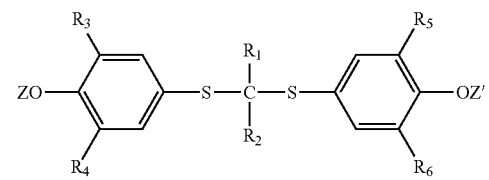

where $R_1$, $R_2$, $R_3$, $R_4$, $R_5$, $R_6$, Z and Z' are defined herein.

12 Claims, No Drawings

PROCESS FOR PREPARATION OF PROBUCOL DERIVATIVES

FIELD OF INVENTION

The present invention relates to 4,4'-(isopropylidenedithio)bis[2,6-di-tert-butylphenol], known and referred to herein by its generic name "probucol", and to derivatives of probucol. More particularly, this invention relates to an improved process for the preparation of probucol derivatives.

BACKGROUND OF THE INVENTION

Probucol is a well-known antioxidant that is related to antioxidant compounds such as 2-(3)-tertiary butyl-4-hydroxyanisole, 2,6-di-tertiary butyl-4-methylphenol and the like. These compounds are used in food and food products to prevent oxidative deterioration.

Probucol is represented by the following structural formula

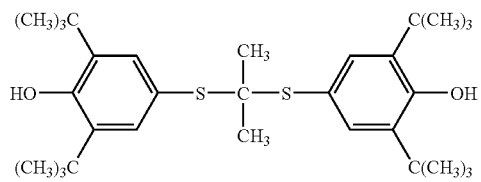

The preparation of this compound is a multistep process, typically starting by reacting a solution of the appropriately-substituted 4-mercaptophenol with acetone, in the presence of a catalytic amount of a strong acid. Probucol precipitates from the reaction mixture and is readily separated and purified. The reaction is described in detail in U.S. Pat. No. 3,862,332 (Barhhart et al).

Similarly, probucol and certain of its derivatives are also described in U.S. Pat. No. 3,485,843 (Wang), U.S. Pat. No. 3,576,833 (Neuworth) and U.S. Pat. No. 4,985,465 (Handler).

Probucol and its derivatives possess pharmaceutical properties that include antiatherogenesis, lipid lowering and the like. But probucol and numerous of its derivatives are poorly soluble in body fluids.

In order to avoid the low water solubility problems associated with probucol utilization in the body, more water-soluble derivatives have been prepared. Thus, U.S. Pat. No. 5,262,439 (Parthasarathy) discloses a class of water-soluble probucol derivatives having one or more ester groups replacing the phenolic hydroxyl group of the probucol molecule. Some of the compounds disclosed in this reference have polar or charged functionalities attached to the ester group, e.g., the groups carboxylic acid, amide, amino, and aldehyde. The method disclosed for preparing these water-soluble probucol compounds involves the reaction of probucol with the carboxylic acid anhydride compound bearing the desired polar or charged functionality in the presence of a catalyst.

Similarly, U.S. Pat. Nos. 6,323,359 and 6,548,699 also disclose water soluble derivatives of probucol. The compounds set forth in U.S. Pat. No. 6,323,359 are produced by a process involving the reaction of a probucol dianion with carboxylic acid anhydrides. The compounds disclosed in U.S. Pat. No. 6,548,699 are synthesized by reaction of probucol with, inter alia, halo-substituted aliphatic esters.

The prior art processes are disadvantageous, since they are not effective in producing the desired alkylated derivatives of probucol in any appreciable yields.

Accordingly, it is desirable to have available a process to efficiently prepare probucol derivatives in high yields.

SUMMARY OF THE INVENTION

The process of the present invention is an improvement in a process to produce water soluble derivatives of probucol. The prior art process comprises the reaction of a solution of probucol with a carboxylic acid anhydride such as succinic acid anhydride, glutaric acid anhydride, adipic acid anhydride, suberic acid anhydride, sebacic acid anhydride, azelaic acid anhydride, phthalic acid anhydride or maleic acid anhydride in the presence of an alkali metal or ammonium hydroxide or alkoxide for a time and at a temperature sufficient to form a reaction mixture of dicarboxylic acid-substituted derivatives of probucol. These water soluble probucol derivatives are then separated from said reaction mixture.

The improved process comprises adding to the reaction mixture an aqueous solution of a $C_1$ to $C_8$ alkyl alcohol thereby precipitating unreacted probucol from said reaction mixture. The precipitated probucol is separated and the reaction is repeated using said precipitated probucol.

DESCRIPTION OF THE PREFERRED EMBODIMENTS

The present invention provides an improved process for preparing certain water soluble probucol derivatives.

As used herein, the term "$C_1$ to $C_8$ alkyl" is intended to mean and include the groups that are $C_1$ to $C_8$ linear or branched alkyl which include the moieties methyl, ethyl, n-propyl, isopropyl, isobutyl, sec-butyl, tert-butyl, n-pentyl, 2-methylpentyl, n-heptyl, n-octyl and the like.

The term "$C_6$ to $C_{12}$ aryl" is intended to mean and include the aromatic radicals having 6 to 12 carbon atoms in the aromatic ring system that may be substituted or unsubstituted one or more times by alkyl, nitro or halo which includes phenyl, naphthyl, phenanthryl, anthracenyl, thienyl, pyrazolyl and the like.

The term "$C_3$ to $C_6$ alkenyl" is intended to mean and include the groups that are $C_3$ to $C_6$ linear or branched alkenyl which include the moieties 1-propenyl, 1-butenyl, 2-butenyl, 1-pentenyl, 2-pentenyl and the like.

The term "alkali metal" is intended to mean those metals in Group I and Ia of the Periodic Table of the Elements such as lithium, potassium, sodium and the like.

The water-soluble derivatives of the probucol compounds herein are obtained by reaction of one or both of the hydroxyl groups of probucol or the probucol derivative with a compound that forms an alkali metal or ammonium salt of probucol, i.e., the alkali metal or ammonium substitutes for hydrogen at one or both of probucol's hydroxyl groups. The compounds that form these salts are strongly basic reactants. They are illustrated by the alkali metal hydrides, alkali metal hydroxides, alkali metal alkoxides, alkyl ammonium alkoxides or alkyl ammonium hydroxides. Mixtures of these compounds are also useful in producing the desired probucol salts. Potassium is the most preferred alkali metal of these strongly basic reactants used in this step. The process is disclosed in U.S. Pat. No. 6,323,359, incorporated herein by reference. The process is described in the specification herein below.

This first reaction of the prior art process to synthesize water soluble derivatives of probucol or probucol compounds produces a mixture of mono- and dianions of the following Formula 1 (where each A may a proton, an alkali metal cation or an ammonium cation)

Formula 1

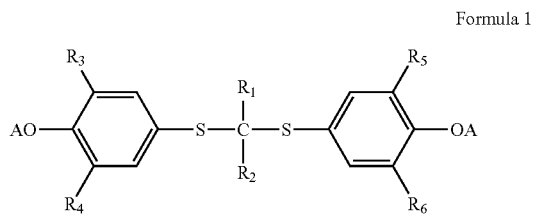

where $R_1$ and $R_2$ are the same or different and are alkyl, alkenyl or aryl having from 1 to 8 carbon atoms and $R_3$, $R_4$, $R_5$ and $R_6$ are the same or different and are alkyl having from 1 to 4 carbon atoms.

Preferably, $R_1$ and $R_2$ are the same and are alkyl having from 1 to 6 carbon atoms, most preferably methyl.

Preferably $R_3$, $R_4$, $R_5$ and $R_6$ are the same and are alkyl having from 1 to 4 carbon atoms, most preferably tert-butyl The mixture of mono- and dialkali metal or ammonium salt of the probucol derivative readily forms and may be removed from the reaction solution as a solid (by precipitation and filtration, etc.) and subsequently used in the second step of the prior art process, or the reaction solution resulting from the first step of the reaction can be used "as is" for the second step, i.e., without separating the mixture of mono- and dianions. In either case, the salt produced in the first step is treated with the acid anhydride which reacts with at least one of the alkali metal or ammonium probucol phenolates. However, it should be noted that because there are two reactive sites available in the mono- and dianionic mixture, either one or both of these sites can be substituted by the incoming acid anhydride moiety.

The subsequent reaction of the compounds of Formula 1 with an acid anhydride such as succinic acid anhydride, glutaric acid anhydride, adipic acid anhydride, suberic acid anhydride, sebacic acid anhydride, azelaic acid anhydride, phthalic acid anhydride or maleic acid anhydride produces the compounds of the Formula 2 below Formula 2

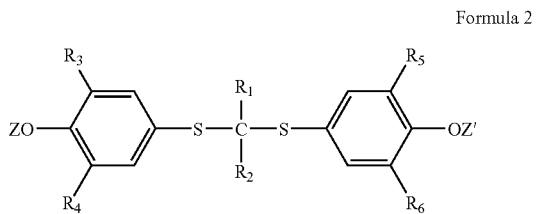

where Z and Z' are the same or different and are hydrogen, or the moiety —C(O)—$C_1$ to $C_6$ alkyl C(O)OA or the moiety —C(O)—$C_3$ to $C_6$-alkenyl C(O)OA where A is an alkali metal or ammonium cation and alkyl and alkenyl are as previously defined, with the proviso that Z and Z' can not both be hydrogen.

As noted, two probucol derivatives may be formed, i.e., the desired mono substitution product, where Z and Z' are different and are hydrogen and the moiety —C(O)—$C_1$ to $C_6$-alkyl C(O)OA or the moiety —C(O)—$C_3$ to $C_6$ alkenyl-C(O)OA where A is an alkali metal or ammonium cation and alkyl, and alkenyl are as previously defined or the disubstitution product, where Z and Z' are the same and are the moiety the moiety —C(O)—$C_1$ to $C_6$-alkyl C(O)OA or the moiety —C(O)—$C_3$ to $C_6$ alkenyl-C(O)OA where A is an alkali metal or ammonium cation and alkyl, and alkenyl are as previously defined.

The reaction mixture to produce the compounds of Formula 2 has a pH of from about 9 to about 14 and typically contains the unreacted probucol or probucol derivative as well as the mono and di substitution products of Formula 2.

The improvement in the prior art process discussed herein relates specifically to the recovery and reuse (recycle) of the unreacted probucol or probucol derivative.

The reaction mixture produced in the second step of the reaction as described above is treated with an aqueous solution of a $C_1$ to $C_8$ linear or branched aliphatic alcohol. After such treatment, the unreacted probucol or probucol derivative precipitates from the reaction solution and is separated by any conventional means, i.e., filtration, centrifugation, etc. The reaction is then repeated using this probucol that was precipitated and separated from the reaction mixture. The filtrate, which contains the mono- and di-substitution products disclosed above is further treated to recover the desired water soluble derivatives of probucol or probucol compounds.

The alcohols of use to effect the precipitation of the unreacted probucol or probucol derivative are, for example, methyl alcohol, ethyl alcohol, n-propyl alcohol, isopropyl alcohol, n-butyl alcohol, sec-butyl alcohol, tert-butyl alcohol, n-pentyl alcohol, 2-methylpentyl alcohol, n-heptyl alcohol, n-octyl alcohol and the like. Preferably the alcohols used in the improved process of the present invention are methyl alcohol, ethyl alcohol, n-propyl alcohol, and isopropyl alcohol, most preferably methyl alcohol.

The precipitation is carried for a time and at a temperature sufficient to precipitate substantially all of the unreacted probucol or probucol derivative in the reaction mixture, preferably from about 30 minutes to about 2 hours at about 25° to about 50° C., most preferably from about 30 minutes to about 45 minutes at about 25° to about 30° C.

As a further improvement in the prior art process to synthesize water solution derivatives of probucol or probucol compounds, the solution of the compounds of Formula 2, i.e., the solution that remains after removal of the unreacted probucol or probucol derivative as disclosed above, is treated with an aqueous solution of phosphoric acid, typically a 75% aqueous solution, for a time and at a temperature sufficient to react with and protonate the alkali metal or ammonium salts of the probucol or probucol derivative, usually from about 30 minutes to about 2 hours at 50° to about 100° C., most preferably for about 30 minutes at 60° C.

The alkali metal or ammonium phosphate salt precipitates from the reaction solution is removed by conventional means , i.e., filtration, etc. Upon cooling to about 5° C. to about 25° C., the protonated mono substitution product, where Z and Z' are different and are hydrogen and the moiety —$C_1$ to $C_6$-alkyl C(O)OH or the moiety —C(O)—$C_3$ to $C_6$ alkenyl-C(O)OH where alkyl, and alkenyl are as previously defined and the disubstitution product where Z and Z' are the same and are hydrogen and the moiety —$C_1$ to $C_6$-alkyl C(O)OH or the moiety —C(O)—$C_3$ to $C_6$ alkenyl-C(O)OH where alkyl, and alkenyl are as previously defined precipitate from the reaction mixture; while the alkali or ammonium phosphate salt remains dissolved in the reaction mixture. The mono and disubstitution products are separated by any conventional means, i.e., by filtration, centrifugation, etc.

An organic hydrocarbon solvent having the formula $C_nH_{2n+2}$ where n is an integer from 5 to 12 is next added to the separated solid mixture of the mono substitution product, where Z and Z' are different and are hydrogen and the moiety —C(O)—$C_1$ to $C_6$-alkyl C(O)OH or the moiety —C(O)—$C_3$ to $C_6$ alkenyl-C(O)OH where alkyl, and alkenyl are as previously defined and the disubstitution product, where Z and Z' are the same and are the moiety the moiety —C(O)—$C_1$ to $C_6$-alkyl C(O)OH or the moiety —C(O)—$C_3$ to $C_6$ alkenyl-C(O)OH where alkyl, and alkenyl are as previously defined.

The hydrocarbon solvent preferentially dissolves the compounds of Formula 2 where Z and Z' are different and are hydrogen and the moiety C(O)—$C_1$ to $C_6$-alkyl C(O)OH or the moiety —C(O)—$C_3$ to $C_6$ alkenyl-C(O)OH where alkyl, and alkenyl are as previously defined. The compounds of Formula 2 where Z and Z' are the same and are the moiety C(O)—$C_1$ to $C_6$-alkyl C(O)OH or the moiety —C(O)—$C_3$ to $C_6$ alkenyl-C(O)OH where alkyl, and alkenyl are as previously defined and are removed from the reaction mixture by conventional means, i.e., filtration, etc. leaving a solution of the desired mono-substituted probucol or probucol derivative.

It is preferred that the integer n of the hydrocarbon solvent is 6 to 9, Most preferably the hydrocarbon solvent is hexane, heptane or octane.

The formation of the acidified solution of the compounds of Formula 2 using the hydrocarbon solvent is carried out at temperatures >40° C. but not above 150° C. Preferably the temperature of the solvent-forming solution is about 45° to about 85° C.

The mono-substituted crystalline probucol or probucol derivative may be obtained from the solution by conventional separation processes such as by distilling the solvent or by cooling and separation of the precipitated solid by centrifugation or by filtration or by other conventional means.

The present invention is described in detail in the examples set forth below which are provided by way of illustration only and therefore should not be considered as limiting the scope of the invention.

EXAMPLES

Synthesis of Water Soluble Derivatives of Probucol

General Process

Example 1

In an appropriately sized vessel, probucol (1 equivalent) and acetone (60 weight percent) are combined. With agitation potassium tert-butoxide (0.67 equivalent) is charged and the resultant solution warmed to ~45° C. for about 60 minutes. Succinic anhydride (0.67 equivalent) is charged and the system stirred at ~40° C. for at least 30 minutes. A dark reaction mixture forms which contains a combination of the salts of di-succinylated probucol (DSP), mono-succinylated probucol (MSP) and unreacted probucol (PRO). The ratio of DSP:MSP:PRO is about 4:29:67.

Specific Process

Example 1

Preparation and Purification of Monosuccinylated Probucol (MSP)

In an appropriate-sized vessel, probucol (500 g, 0.97 mol) and acetone (300 g) are combined. With agitation potassium tert-butoxide (73 g, 0.65 mol) is charged and the resultant solution warmed to ~40° C. for at least 45 minutes. Succinic anhydride (65 g, 0.65 mol) is charged and the system stirred at ~45° C. for at least 60 minutes. A dark reaction mixture forms which contains a combination of the salt of di-succinylated probucol (DSP), the salt of mono-succinylated probucol (MSP) and unreacted probucol.

Methanol Precipitation of Probucol

To the resultant dark reaction mixture is added 1 liter of methanol. After agitation for 10 minutes, 175 mL of 45% potassium hydroxide is added and the solution heated to about 55° C. The temperature is maintained at about 55° C. and 1750 mL of water is added over 60 minutes. When the water addition is completed, the solution is allowed to cool to about 20° C. where probucol precipitates from the resulting solution. The crystalline probucol is removed by filtration, washed with 1:1 methanol:water and dried under vacuum at 65° C. Analysis of the recovered probucol was as follows: MSP 3%, probucol 97%. This recovered probucol was used in the reaction reported below, Example 2.

Phosphoric Acid Treatment

After the removal of the solid probucol precipitate, 500 mL of n-heptane is added to the filtrate and the mixture is agitated for 30 minutes. After allowing the phases to separate, the n-heptane phase is discarded and the aqueous phase (which contains the potassium salts of MSP and DSP) is treated with 175 mL of 75% aqueous phosphoric acid at 0-25° C. The precipitated solids, which are a mixture of MSP and DSP, are removed by centrifugation and washed with 250 mL of water. The centrifuged solids are added to a solution of 79 mL of 75% phosphoric acid and 357 mL of water and agitated for 15 minutes. The slurry is centrifuged and the centrifuged solids are washed with 250 mL of water and dried at 80° C. for about 2 hours. Analysis of the solids is as follows: DSP 10; MSP 89; and probucol 1.

MSP Extraction 1

The dried solids are stirred with 1 L of n-heptane at 80° C. for 60 minutes and the slurry filtered while hot. The DSP laden solids are filtered and retained for the subsequent extraction step.

The filtrate, which contains the desired MSP, is cooled to about 25° C. Crude MSP precipitates and is removed by filtration, while the mother liquor (Mother Liquor 1) is retained for the next extraction.

MSP Extraction 2

The DSP laden solids from Extraction 1 are combined with the mother liquor (Mother Liquor 1) and enough n-heptane is added to bring the total solvent volume to 1 L. The slurry is heated to 80° C. for 60 minutes with agitation and filtered while still hot. After cooling to about 25° C., the precipitated solids (crude MSP) are filtered and the filtrate (Mother Liquor 2) is used in the next extraction.

MSP Extraction 3

The DSP laden solids from Extraction 2 are combined with the mother liquor (Mother Liquor 2) and enough n-heptane is added to bring the total solvent volume to 1 L. The slurry is heated to 80° C. for 60 minutes with agitation and filtered while still hot. After cooling to about 25° C., the precipitated solids (crude MSP) are filtered.

The crude MSP solids obtained from Extraction steps 1, 2 and 3 are combined and dried at about 65° C. under vacuum to provide 120 g of white solids. Analysis of the crude products is as follows: DSP 1.7: MSP 97.3; probucol 0.4.

Example 2

Preparation of Monosuccinylated Probucol by Probucol Recycle

Example 1 was repeated, using 350 g of recovered probucol from Example 1. The amount of probucol recovered after the methanol precipitation step was 267 g having the following composition: MSP 3.0, probucol 96.9.

The phosphoric acid treatment of the filtrate was repeated as shown in Example 1, and 1 after the three extraction steps 102 g of crude product was obtained having the following analysis: DSP 10.3, MSP 88.7 probucol 0.5.

We claim:

1. In a process for the preparation of a water-soluble derivative of probucol having the following formula Formula 2

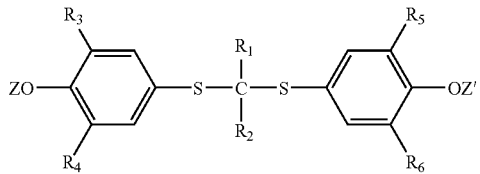

where $R_1$ and $R_2$ are the same or different and are —$C_1$-$C_6$ alkyl, —$C_3$-$C_6$ alkenyl or aryl, $R_3$, $R_4$, $R_5$ and $R_6$ are the same or different and are $C_1$-$C_6$ alkyl, Z and Z' are the same or different and are hydrogen or the groups that are saturated acyl or unsaturated acyl having from 1 to 8 carbon atoms said saturated acyl or unsaturated acyl containing a polar or charged functionality where Z and Z' can not both be hydrogen by the reaction of a probucol compound of the formula

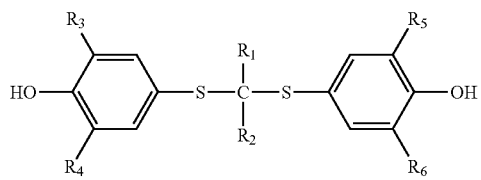

where $R_1$, $R_2$, $R_3$, $R_4$, $R_5$ and $R_6$ are as previously defined with a compound selected from the group consisting of alkali metal hydroxide, alkali metal alkoxide, alkyl ammonium hydroxide, alkyl ammonium alkoxide and mixtures thereof to form an alkali metal or ammonium salt of said probucol compound and reacting said salt with a carboxylic acid anhydride selected from the group consisting of succinic acid anhydride, glutaric acid anhydride, adipic acid anhydride, suberic acid anhydride, sebacic acid anhydride, azelaic acid anhydride, phthalic acid anhydride or maleic acid anhydride to form a reaction mixture and separating said water soluble probucol derivative from said reaction mixture an separating the water soluble derivative of probucol, the improvement comprising 1—adding to the reaction mixture an aqueous solution of a $C_1$ to $C_8$ alkyl alcohol thereby precipitating unreacted probucol from said reaction mixture, 2—separating the precipitated probucol from said reaction mixture and 3—repeating said reaction using said precipitated probucol "wherein the improvement is effective for producing probucol derivatives of Formula 2 more efficiently in higher yields.

2. The process according to claim 1 wherein the $C_1$ to $C_8$ alkyl alcohol is selected from the group consisting of methyl alcohol, ethyl alcohol, n-propyl alcohol, isopropyl alcohol, n-butyl alcohol, sec-butyl alcohol, tert-butyl alcohol, n-pentyl alcohol, 2-methylpentyl alcohol, n-heptyl alcohol, n-octyl alcohol and mixtures thereof.

3. The process according to claim 2 wherein said alcohol is methyl alcohol, ethyl alcohol, n-propyl alcohol or isopropyl alcohol.

4. The process according to claim 3 wherein said alcohol is methyl alcohol.

5. The process according to claim 1 wherein the addition is carried out over a period of from about 30 minutes to about 2 hours at about 25° to about 50° C.

6. The process according to claim 5 wherein the addition is carried out over a period of from about 30 minutes to about 45 minutes at about 25° to about 30° C.

7. In a process for the preparation of a water-soluble derivative of probucol having the following formula Formula 2

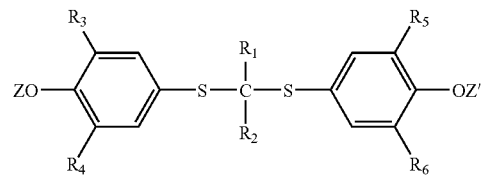

where $R_1$ and $R_2$ are the same or different and are —$C_1$-$C_6$ alkyl, —$C_3$-$C_6$ alkenyl or aryl, $R_3$, $R_4$, $R_5$ and $R_6$ are the same or different and are $C_1$-$C_6$ alkyl, Z and Z' are the same or different and are hydrogen or the groups that are saturated acyl or unsaturated acyl having from 1 to 8 carbon atoms said saturated acyl or unsaturated acyl containing a polar or charged functionality where Z and Z' can not both be hydrogen by the reaction of a probucol compound of the formula

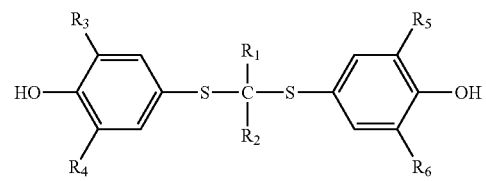

where $R_1$, $R_2$, $R_3$, $R_4$, $R_5$ and $R_6$ are as previously defined with a compound selected from the group consisting of alkali metal hydroxide, alkali metal alkoxide, alkyl ammonium hydroxide, alkyl ammonium alkoxide and mixtures thereof to form an alkali metal or ammonium salt of said probucol compound and reacting said salt with a carboxylic acid anhydride selected from the group consisting of succinic acid anhydride, glutaric acid anhydride, adipic acid anhydride, suberic acid anhydride, sebacic acid anhydride, azelaic acid anhydride, phthalic acid anhydride or maleic acid anhydride to form a reaction mixture and separating said water soluble probucol derivative from said reaction mixture an separating the water soluble derivative of probucol, the the improvement comprising 1—adding phosphoric acid to said aqueous phase to form a reaction mixture thereby forming a solid mixture of a compound of Formula 2 where Z and Z' are different and are hydrogen and the moiety $C(O)$—$C_1$ to $C_6$-alkyl $C(O)OH$ or the moiety —$C(O)$—$C_3$ to $C_6$ alkenyl-$C(O)OH$ where alkyl and alkenyl are as previously defined and a compound of Formula 2 where Z and Z' are the same and are the moiety $C(O)$—$C_1$ to $C_6$-alkyl $C(O)OH$ or the moiety —$C(O)$—$C_3$ to $C_6$ alkenyl-$C(O)OH$ where alkyl and alkenyl are as previously defined;

2—adding to said reaction mixture an organic hydrocarbon having the formula $C_nH_{2n+2}$ where n is an integer from 5 to 12 thereby forming an aqueous phase and a $C_nH_{2n+2}$ hydrocarbon phase, 3—separating said $C_nH_{2n+2}$ hydrocarbon phase and 4—obtaining said water soluble derivative of probucol from said $C_nH_{2n+2}$ hydrocarbon phase "wherein the improvement is effective for producing probucol derivatives of Formula 2 more efficiently in higher yields.

8. The process according to claim 7 wherein said phosphoric acid is a 75% aqueous solution of phosphoric acid.

9. The process according to claim 8 wherein n of the organic hydrocarbon is an integer of from 6 to 9.

10. The process according to claim 9 wherein said organic hydrocarbon is n-hexane, n-heptane or n-octane.

11. The process according to claim 7 wherein said solid mixture in step 2 is at a temperature of >40° C. but not above 150° C.

12. The process according to claim 11 wherein said solid mixture in step 2 is at a temperature of about 45° to about 85° C.

* * * * *